(12) United States Patent
Lee et al.

(10) Patent No.: US 10,274,552 B2
(45) Date of Patent: *Apr. 30, 2019

(54) METHOD AND APPARATUS FOR PROVIDING CONTENT RELATED TO CAPTURE OF A MEDICAL IMAGE

(71) Applicant: SAMSUNG ELECTRONICS CO., LTD., Suwon-si (KR)

(72) Inventors: Dae-ho Lee, Seongnam-si (KR); Sang-young Zho, Seoul (KR); Joon-soo Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/613,550

(22) Filed: Jun. 5, 2017

(65) Prior Publication Data

US 2017/0269173 A1  Sep. 21, 2017

Related U.S. Application Data

(63) Continuation of application No. 14/454,992, filed on Aug. 8, 2014, now Pat. No. 9,753,103.

(30) Foreign Application Priority Data

Aug. 9, 2013 (KR) ........................ 10-2013-0094900

(51) Int. Cl.
*A61B 5/00* (2006.01)
*A61B 6/00* (2006.01)
(Continued)

(52) U.S. Cl.
CPC ............ *G01R 33/283* (2013.01); *A61B 5/055* (2013.01); *A61B 5/4884* (2013.01); *A61B 6/46* (2013.01);
(Continued)

(58) Field of Classification Search
CPC ......... A61B 5/055; A61B 5/4884; A61B 6/46; A61M 21/02
See application file for complete search history.

(56) References Cited

U.S. PATENT DOCUMENTS 5,709,207 A * 1/1998 Duerk .................. G01R 33/283
                                                    324/307
5,794,621 A * 8/1998 Hogan ................... A61B 5/055
                                                    600/407

(Continued)

FOREIGN PATENT DOCUMENTS

EP  2649935 A2  10/2013
JP  H 7-241285 A  9/1995

(Continued)

OTHER PUBLICATIONS

Communication dated Apr. 3, 2017, from the European Patent Office in counterpart European Application No. 14180528.3.

(Continued)

*Primary Examiner* — Baisakhi Roy

(74) *Attorney, Agent, or Firm* — Sughrue Mion, PLLC

(57) ABSTRACT

Disclosed is a method of providing content related to capture of a medical image of an object. The method includes acquiring at least one of information related to a state of the object and information related to a capture protocol, determining content to be provided to the object on a basis of the acquired information, and outputting the determined content.

20 Claims, 13 Drawing Sheets

(51) Int. Cl.
*A61B 5/055* (2006.01)
*A61M 21/02* (2006.01)
*G01R 33/28* (2006.01)
*G01R 33/48* (2006.01)
*G01N 24/08* (2006.01)
*G01R 33/56* (2006.01)
*A61M 21/00* (2006.01)

(52) U.S. Cl.
CPC ............ *A61B 5/7285* (2013.01); *A61M 21/02* (2013.01); *A61M 2021/0027* (2013.01); *A61M 2021/0044* (2013.01); *G01N 24/081* (2013.01); *G01R 33/4806* (2013.01); *G01R 33/4828* (2013.01); *G01R 33/5605* (2013.01)

(56) References Cited

U.S. PATENT DOCUMENTS

| | | | |
|---|---|---|---|
| 8,358,734 B2 | 1/2013 | Nakamura et al. | |
| 8,805,476 B2 | 8/2014 | Yang | |
| 9,232,908 B2* | 1/2016 | Sugiura | A61B 5/0263 |
| 9,753,103 B2* | 9/2017 | Lee | G01R 33/283 |
| 2004/0059213 A1* | 3/2004 | Kassai | A61B 5/055 |
| | | | 600/410 |
| 2005/0049493 A1* | 3/2005 | Kerby | A61B 8/00 |
| | | | 600/437 |
| 2005/0083054 A1* | 4/2005 | Feiweier | G01R 33/5659 |
| | | | 324/307 |
| 2005/0235422 A1 | 10/2005 | Wallace | |
| 2006/0241374 A1* | 10/2006 | George | G01R 33/4806 |
| | | | 600/410 |
| 2007/0167724 A1 | 7/2007 | Gadagkar et al. | |
| 2007/0201613 A1* | 8/2007 | Lu | A61N 5/1049 |
| | | | 378/65 |
| 2008/0089463 A1 | 4/2008 | Nakamura et al. | |
| 2008/0281186 A1* | 11/2008 | Kuhara | A61B 5/055 |
| | | | 600/413 |
| 2010/0268061 A1* | 10/2010 | Porter | G01R 33/4806 |
| | | | 600/410 |
| 2011/0084694 A1* | 4/2011 | Waffenschmidt | G01R 33/283 |
| | | | 324/318 |
| 2012/0019245 A1* | 1/2012 | Reddy | G01R 33/5601 |
| | | | 324/309 |
| 2012/0075530 A1 | 3/2012 | Miyazaki et al. | |
| 2012/0220858 A1* | 8/2012 | Carroll | G01R 33/5616 |
| | | | 600/420 |
| 2013/0218004 A1* | 8/2013 | Yang | G01R 33/283 |
| | | | 600/415 |
| 2014/0035578 A1* | 2/2014 | Song | G01V 3/32 |
| | | | 324/309 |
| 2014/0088984 A1* | 3/2014 | Oh | G01R 33/543 |
| | | | 705/2 |
| 2014/0171729 A1 | 6/2014 | Bourne et al. | |
| 2014/0253116 A1* | 9/2014 | Freedman | G01R 33/30 |
| | | | 324/303 |

FOREIGN PATENT DOCUMENTS

| | | |
|---|---|---|
| JP | 2004160086 A | 6/2004 |
| JP | 2008-119449 A | 5/2008 |
| JP | 2010-213773 A | 9/2010 |
| JP | 2012-187166 A | 10/2012 |
| KR | 1020130027656 A | 3/2013 |
| WO | 97/34527 A1 | 9/1997 |
| WO | 2008/062384 A1 | 5/2008 |
| WO | 2009147608 A1 | 12/2009 |
| WO | 2013/153798 A1 | 10/2013 |

OTHER PUBLICATIONS

Communication dated Nov. 3, 2016, issued by the European Patent Office in counterpart European Patent Application No. 16161622.2.
Communication dated May 31, 2016, issued by the Korean Intellectual Property Office in counterpart Korean Application No. 10-2016-0052320.
Communication dated Feb. 18, 2016, issued by the Korean Intellectual Property Office in counterpart Korean Application No. 10-2013-0094900.
Communication from the Korean Intellectual Property Office dated Jan. 21, 2015, in a counterpart Korean application No. 10-2013-0094900.
Communication from the European Patent Office dated Mar. 20, 2015, in a counterpart European Application No. 14180528.3.

* cited by examiner

FIG. 7
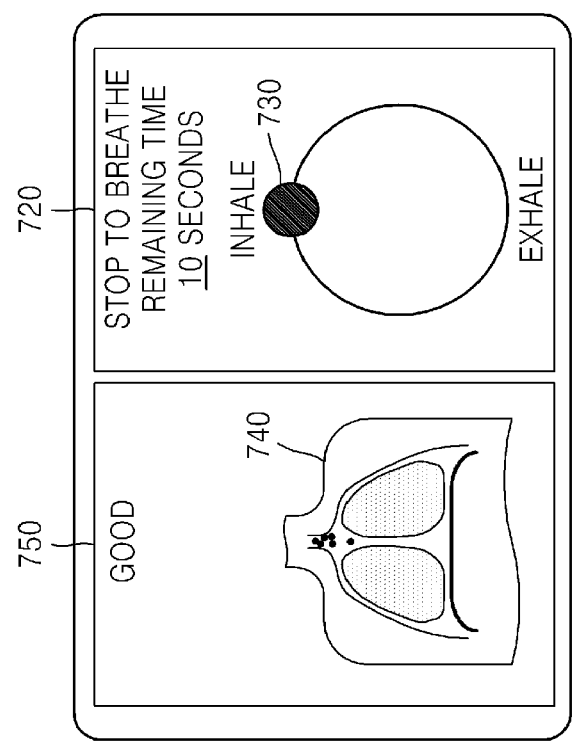
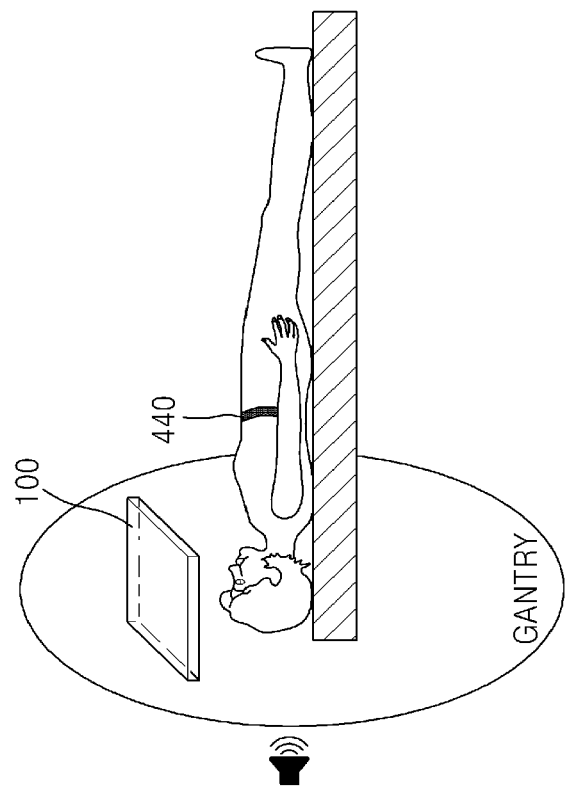

FIG. 8
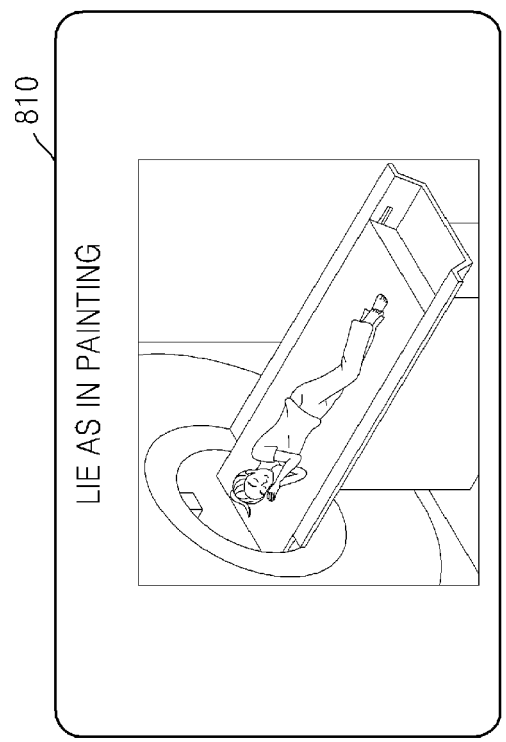
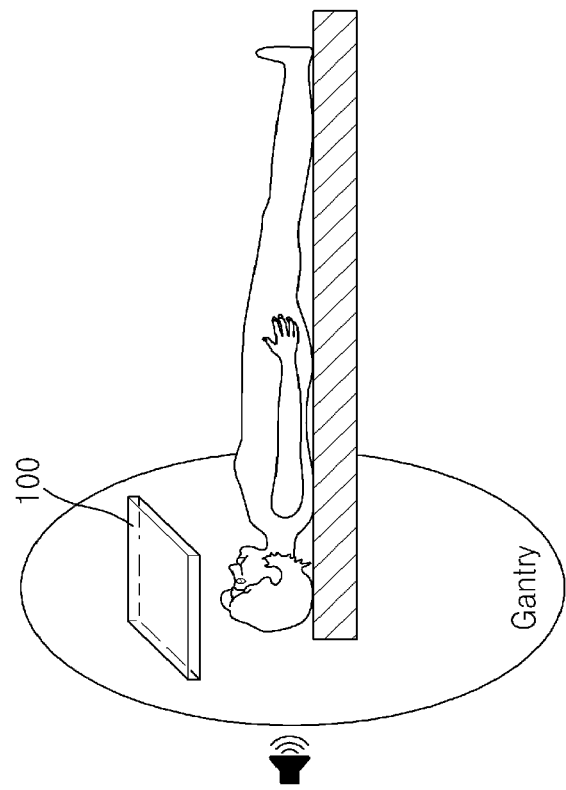

FIG. 11
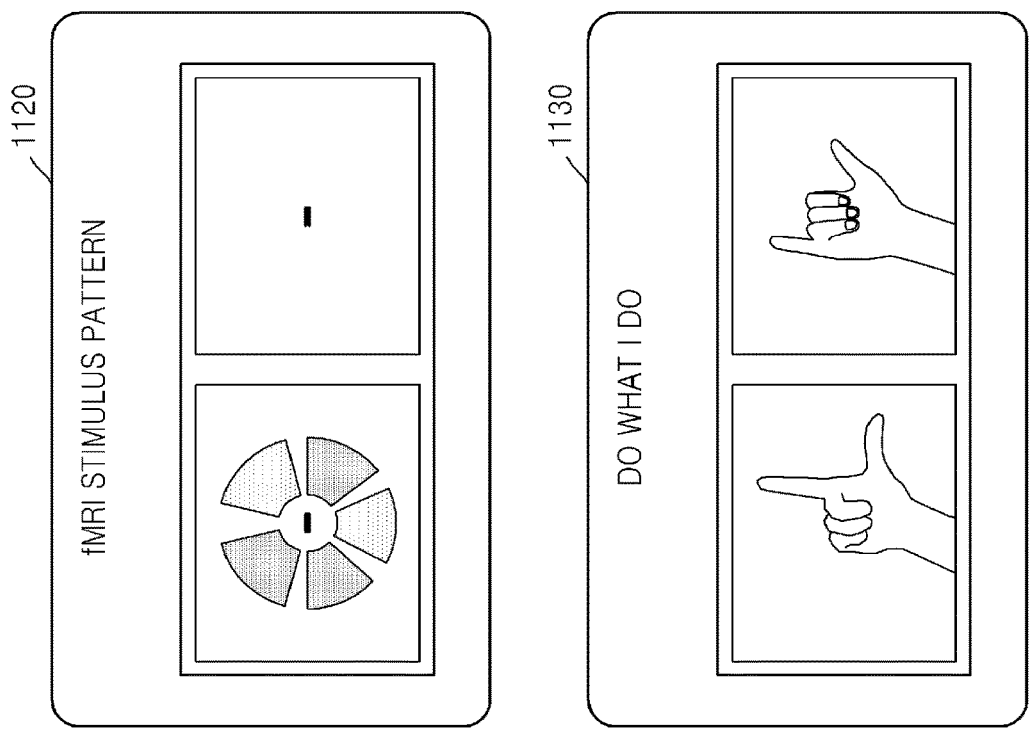
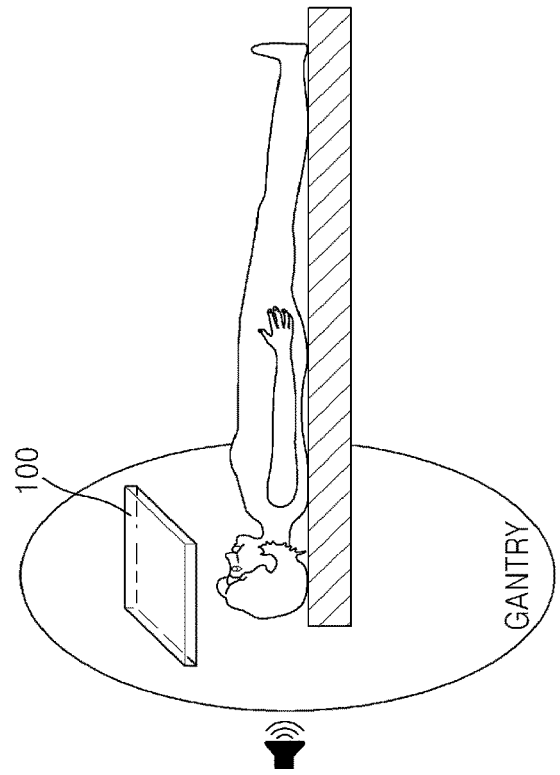

FIG. 12
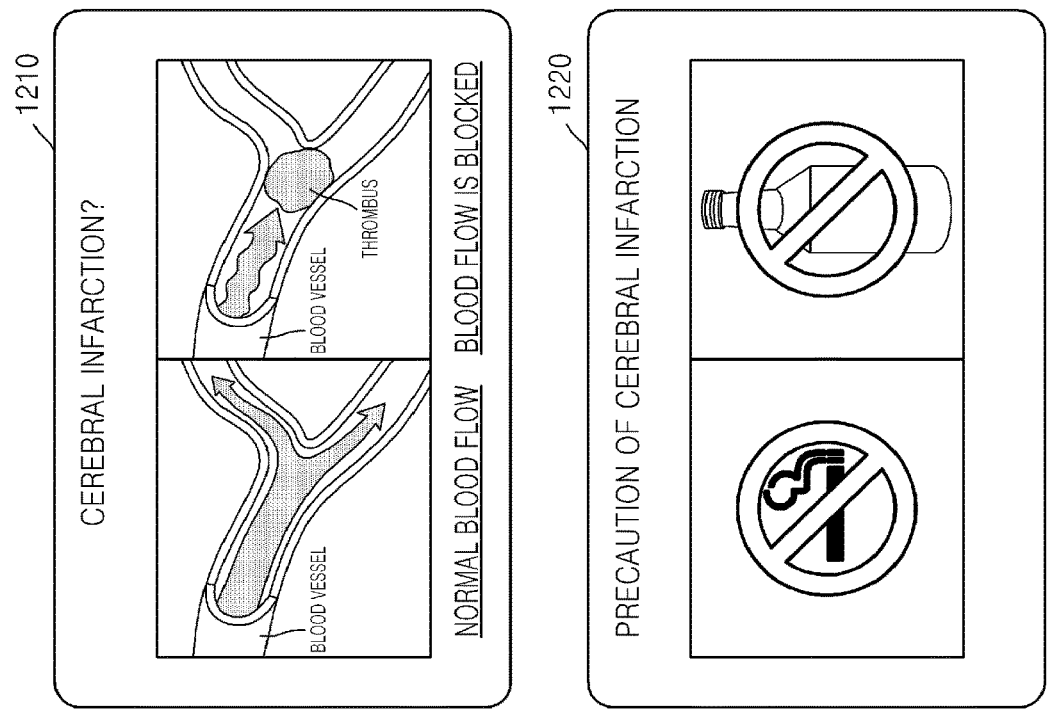
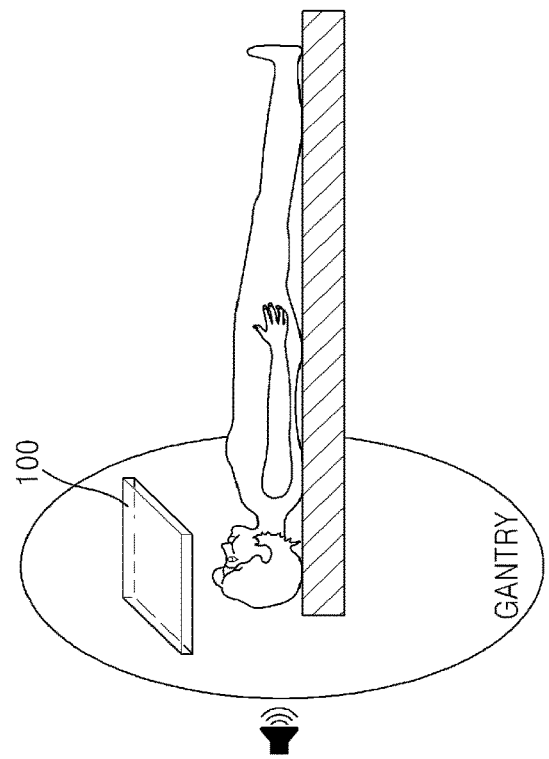

METHOD AND APPARATUS FOR PROVIDING CONTENT RELATED TO CAPTURE OF A MEDICAL IMAGE

RELATED APPLICATIONS

This is a continuation application of U.S. patent application Ser. No. 14/454,992, filed Aug. 8, 2014, in the U.S. Patent and Trademark Office, which claims priority from Korean Patent Application No. 10-2013-0094900, filed on Aug. 9, 2013, in the Korean Intellectual Property Office, the disclosures of which are incorporated herein by reference in their entireties.

BACKGROUND

1. Technical Field

One or more exemplary embodiments relate to a method and apparatus for providing to an object content related to the capture of a medical image.

2. Description of the Related Art

In capturing an object with a medical apparatus such as a magnetic resonance imaging (MRI) apparatus or a computed tomography (CT) apparatus, the object alone lies in a narrow space such as a gantry of the medical apparatus. A user of a medical apparatus communicates with an object by using a microphone and a speaker. However, it is not easy to fully determine a detailed state such as a change in a physical state and a mental state of the object. Therefore, in capturing a medical image, a user of a medical apparatus captures the medical image with no consideration of a detailed state of an object, thus sometimes resulting in a medical accident. In response to capturing an object with a detailed state of the object being accurately determined, an inaccurate medical image is acquired. This results in sometimes having to once again capture the object.

Moreover, a user of a medical apparatus may notify an object of a breathing method or the optimal posture which is required according to the order of capture, through a voice, but when an object is a child or a foreigner, communication may not be smooth. In addition, it is difficult for an object, unskilled in the capture of a medical image, to learn a correct breathing method and the optimal posture in a short time through instruction by a user of a medical apparatus.

SUMMARY

One or more in its entirety embodiments include a method and apparatus for automatically providing content related to the capture of a medical image by using state information or capture information related to an object.

Additional aspects will be set forth in part in the description which follows and, in part, will be apparent from the description, or may be learned by practice of the exemplary embodiments.

According to one or more exemplary embodiments, a method of providing content related to capture of a medical image of an object includes: acquiring at least one of information related to a state of the object and information related to a capture protocol; determining content to be provided to the object on a basis of the acquired information; and outputting the determined content.

The information related to the state of the object includes at least one of information related to a body signal of the object, information related to a posture of the object, information related to a voice of the object, and information related to a motion of the object.

The information related to the body signal includes information related to at least one of a body temperature, a blood pressure, a heart rate, a breath pattern, a brainwave and muscular motion of the object.

The information related to the capture protocol includes information related to at least one of a captured part of the object, a capture direction, a pulse sequence to be used for capture, a capture purpose, precautions for capture, a capture time, and setting information before starting capture.

The determining includes selecting content used to stabilize the breath of the object or content used to guide the breath of the object as content to be provided to the object in response to a breath of the object being irregular.

The determining includes selecting content used to stabilize the heartbeat of the object as content to be provided to the object in response to the heart rate of the object among the information related to the heartbeat of the object being equal to or higher than a predetermined reference value.

The information related to the motion of the object includes information related to at least one of a gesture, which is expressed with at least one of the hands, the feet, the head, the eyes, and fingers of the object, and a change of expression of the object.

The determining includes selecting at least one of content used to display a time remaining until starting capture, content used to guide a breathing method of the object before starting the capture, and content used to guide a posture of the object before starting the capture, on a basis of the setting information before starting capture.

The determining includes selecting content used to guide the breath of the object and required according to the capture protocol.

The determining includes selecting content used to guide the posture of the object and required according to the capture protocol.

The information related to the capture protocol includes information related to a capture protocol used to acquire a functional magnetic resonance (fMR) image of the object, and the determining includes selecting content used to activate the brain of the object, on a basis of the information related to the capture protocol used to acquire the fMR image.

The information related to the capture protocol includes information related to a protocol used to capture an MR image of the object when performing a stress test for the heart of the object, and the determining includes selecting content used to induce the heart rate of the object to increase, on a basis of the information related to the capture protocol.

The information related to the capture protocol includes information related to a capture protocol for an MR image of a sleeping state of the object, and the determining includes selecting content used to induce the object to sleep, on a basis of the information related to the capture protocol.

The outputting includes outputting the determined content by using at least one of an image, a video, sound and text.

According to one or more exemplary embodiments, an apparatus for providing content related to capture of a medical image of an object includes: an information acquirer configured to acquire at least one of information related to a state of the object and information related to a capture protocol; a content determiner configured to determine content to be provided to the object, on a basis of the acquired information; and an output configured to output the determined content.

The information acquirer includes a state information acquirer that acquires information related to the state of the object; and a capture protocol acquirer that acquires the information related to the capture protocol.

In response to a breath of the object being irregular, the content determiner is configured to select content used to stabilize the breath of the object or content used to guide the breath of the object, as content to be provided to the object.

In response to the heart rate of the object among the information related to the heartbeat of the object being equal to or higher than a predetermined reference value, the content determiner is configured to select content, used to stabilize the heartbeat of the object, as content to be provided to the object.

The content determiner is configured to select at least one of content used to display a time remaining until starting capture, content used to guide a breathing method of the object before starting the capture, and content used to guide a posture of the object before starting the capture on a basis of the setting information, before starting capture.

The content determiner is configured to select content used to guide the breath of the object and required according to the capture protocol.

The content determiner is configured to select content used to guide the posture of the object and required according to the capture protocol.

The information related to the capture protocol includes information related to a capture protocol used to acquire a functional magnetic resonance (fMR) image of the object, and the content determiner is configured to select content used to activate the brain of the object, on a basis of the information related to the capture protocol used to acquire the fMR image.

The information related to the capture protocol includes information related to a protocol used to capture an MR image of the object in response to performing a stress test for the heart of the object, and the content determiner is configured to select content used to induce the heart rate of the object to increase, on a basis of the information related to the capture protocol.

The information related to the capture protocol includes information related to a capture protocol for an MR image of a sleeping state of the object, and the content determiner is configured to select content used to induce the object to sleep, on a basis of the information related to the capture protocol.

The output is configured to output the determined content by using at least one of an image, a video, sound and text.

An information acquirer configured to acquire information related to a state of the user and information related to a capture protocol; a content determiner configured to determine content to be provided to the user, on a basis of the acquired information; and an output configured to output the determined content to the user.

An aspect of an exemplary embodiment may provide an apparatus for providing content related to capture of a medical image of a user, the apparatus including: an information acquirer configured to acquire information related to a state of the user and information related to a capture protocol; a content determiner configured to determine content to be provided to the user, on a basis of the acquired information; and an output configured to output the determined content to the user.

According to one or more exemplary embodiments, a non-transitory computer-readable storage medium may store a program for executing the method.

BRIEF DESCRIPTION OF THE DRAWINGS

These and/or other aspects will become apparent and more readily appreciated from the following description of the exemplary embodiments, taken in conjunction with the accompanying drawings in which:

FIG. 7 illustrates a method of providing content used to guide a breath of an object according to a capture protocol, according to an exemplary embodiment;

FIG. 8 illustrates a method of providing content used to guide a posture of an object according to a capture protocol, according to an exemplary embodiment;

FIG. 11 illustrates a method of providing content for functional magnetic resonance imaging (fMRI) capture, according to an exemplary embodiment;

FIG. 12 illustrates a method of providing content related to an object while capturing a medical image, according to an exemplary embodiment;

DETAILED DESCRIPTION

Figure 1:
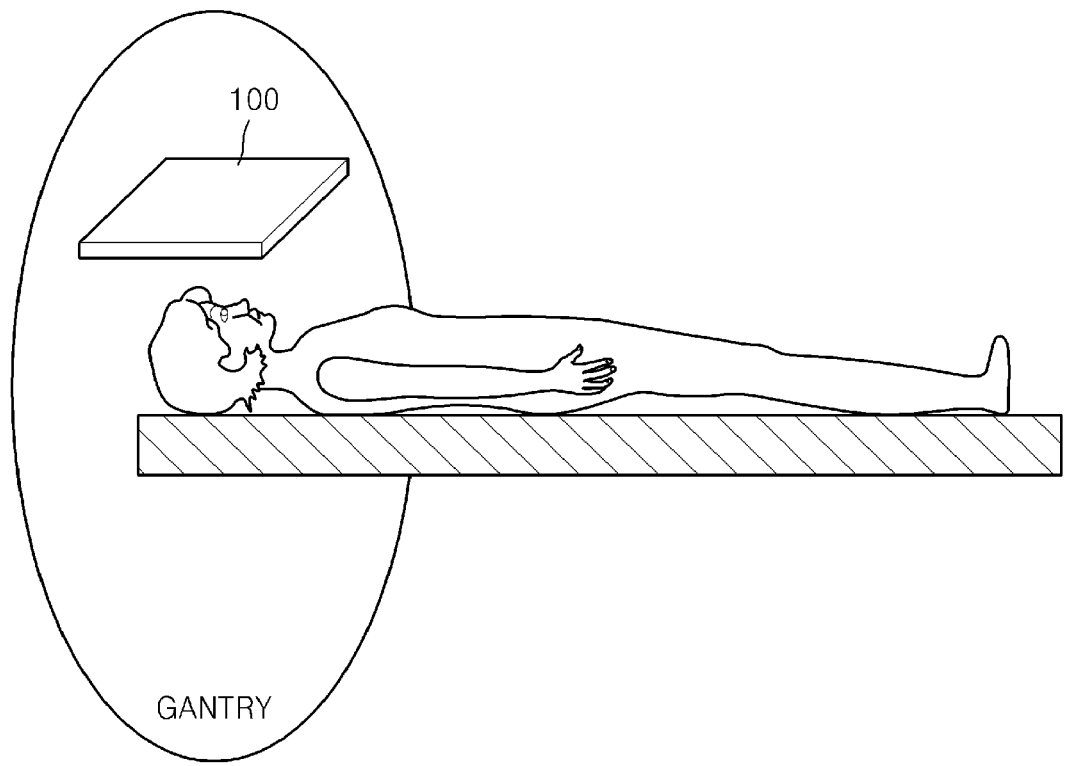
FIG. 1 illustrates a content providing apparatus for providing content to an object, according to an exemplary embodiment.

Reference will now be made in detail to the exemplary embodiments, examples of which are illustrated in the accompanying drawings, wherein like reference numerals refer to like elements throughout. In this regard, the exemplary embodiments may have different forms and should not be construed as being limited to the descriptions set forth herein. Accordingly, the exemplary embodiments are merely described below, by referring to the figures, to explain aspects of the present description. Expressions such as "at least one of," when preceding a list of elements, modify the entire list of elements and do not modify the individual elements of the list.

Terms used herein will be briefly described, and the exemplary embodiments will be described in detail.

Terms used in the exemplary embodiments have been selected as general terms which are widely used at present, in consideration of the functions of the exemplary embodiments, but may be altered according to the intent of an operator skilled in the art, conventional practice, or introduction of new technology. Also, in response to their being a term which is arbitrarily selected by the applicant in a specific case, in which case a meaning of the term will be described in detail in a corresponding description portion of the exemplary embodiments. Therefore, the terms should be defined on the basis of the entire content of this specification instead of a simple name of each of the terms.

In this disclosure below, in a description that comprises (or includes or In this disclosure below, when it is described that one comprises (or includes or has) some elements, it should be understood that it may comprise (or include or has) only those elements, or it may comprise (or include or have) other elements as well as those elements if there is no specific limitation. Moreover, each of terms such as " . . . unit", " . . . apparatus" and "module" described in specification denotes an element for performing at least one function or operation, and may be implemented in hardware, software or the combination of hardware and software.

The term "image" used herein may denote multi-dimensional data composed of discrete image factors (for example, pixels in a two-dimensional (2D) image and pixels in a three-dimensional (3D) image). For example, an image may include a medical image of an object which is acquired by an X-ray apparatus, a CT apparatus, a magnetic resonance imaging (MRI) apparatus, an ultrasonic apparatus, or another medical image photographing apparatus.

Moreover, the term "object" used herein may include a person, an animal, a part of the person, or a part of the animal. For example, an object may include an organ such as a liver, a heart, a womb, a brain, breasts, an abdomen, or the like, or a blood vessel. Also, the term "object" may include a phantom. The phantom denotes a material having a volume that is very close to a density of organisms and an effective atomic number, and may include a spherical phantom having a temper similar to a human body.

Moreover, the term "user" used herein is a medical expert, and may be a doctor, a nurse, a medical technologist, a medical image expert, or the like, or may be an engineer repairing a medical apparatus. However, definition of the user is not limited thereto.

Hereinafter, exemplary embodiments will be described in detail to be easily embodied by those skilled in the art with reference to the accompanying drawings. The present invention may, however, be embodied in many different forms and should not be construed as being limited to the exemplary embodiments set forth herein. In the accompanying drawings, a portion irrelevant to a description of the exemplary embodiments will be omitted for clarity. Moreover, like reference numerals refer to like elements throughout.

According to an exemplary embodiment, a content providing apparatus 100 automatically provides content related to the capture of a medical image to an object on the basis of information related to a state of the object and information related to a capture protocol, thus providing a more convenient and personalized medical image capture environment to a user of the medical apparatus and the object.

FIG. 1 illustrates the content providing apparatus 100 for providing content to an object, according to an exemplary embodiment.

The content providing apparatus 100 according to an exemplary embodiment may determine content necessary for capture on the basis of information related to a state of an object and information related to a capture protocol, and provides the determined content to the object.

Moreover, the content providing apparatus 100 may be connected to a body signal measurer, and on the basis of a body signal of an object that is acquired with the body signal measurer, the content providing apparatus 100 may provide content necessary to capture the object, according to a state of the object. Also, the content providing apparatus 100 may be connected to a voice recognition apparatus, an image recognition apparatus, or a medical image capturing apparatus, and may provide content necessary to capture an object according to a state of the object on the basis of voice information, image information, or medical image of the object.

Moreover, the content providing apparatus 100 may acquire information related to a capture protocol to provide desired content to an object, according to the capture protocol.

Figure 2:
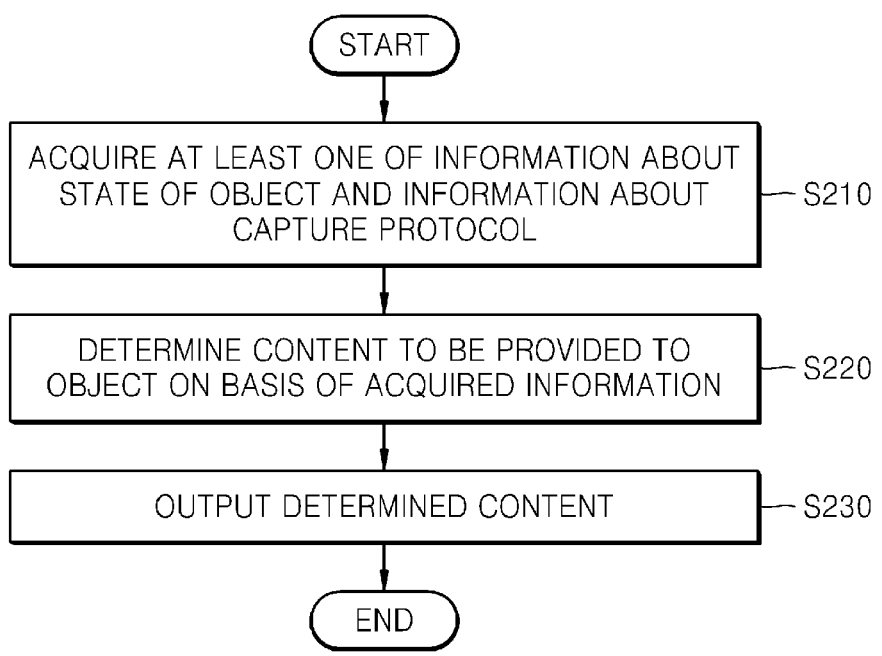
FIG. 2 is a flowchart of a method of providing content related to the capture of a medical image of an object, according to an exemplary embodiment.

FIG. 2 is a flowchart of a method of providing content related to the capture of a medical image of an object, according to an exemplary embodiment.

The method of providing content related to the capture of a medical image of an object, according to an exemplary embodiment, may include operation S210 that acquires at least one of information related to a state of an object and information related to a capture protocol, operation S220 that determines content to be provided to the object on the basis of the acquired information, and operation S230 that outputs the determined content.

According to an exemplary embodiment, the content providing method may acquire at least one of the information related to the state of the object and the information related to the capture protocol in operation S210.

The information related to the state of the object, according to an exemplary embodiment, may include at least one of information related to a body signal of the object, information related to a posture of the object, information related to a voice of the object, and information related to a motion of the object.

The information related to the body signal, according to an exemplary embodiment may include information related to at least one of a body temperature, blood pressure, a heart rate, a breath pattern, a brainwave and muscular motion of the object.

For example, the body temperature of the object may be acquired from a thermometer or a thermal infrared sensor. The blood pressure of the object may be acquired from a blood pressure measurer. Information related to a heartbeat of the object may be acquired from an electrocardiogram (ECG) measurer. The breath pattern of the object may be measured by a breath measurer (respiratory bellows). The brainwave of the object may be measured by a brainwave measurer. In addition, the muscular motion of the object may be measured by an electromyogram (EMG) measurer.

Information related to a motion of an object may include information related to at least one of a gesture, which is expressed with at least one of the hands, the feet, the head, the eyes, and the fingers of the object, and an change of expression of the object.

The content providing apparatus 100 according to an exemplary embodiment may recognize a posture or motion of an object by using an image sensor. The content providing apparatus 100 may analyze the recognized posture or motion of the hands, the feet, the head, the eyes, the fingers, or the like, of the object in order to determine a gesture having a specific meaning. The gesture having the specific meaning may be previously built in a database type. The content providing apparatus 100 may recognize a facial expression of the object, and determine a current mental state of the object by using a previously built database.

The information related to the capture protocol, according to an exemplary embodiment, may include information related to at least one of a captured part of an object, a capture direction, a pulse sequence to be used for capture, a capture purpose, precautions for capture, a capture time, and setting information before starting capture.

The content providing apparatus 100, according to an exemplary embodiment may extract information related to the capture protocol from a database that stores medical image-related information. The database storing the medical image-related information may be built in a picture archiving and communication system (PACS) server, an electronic medical record (EMR) server, a personal health record (PHR) server, and a radiology information system (RIS) server. In other words, the content providing apparatus 100 may extract the information related to the capture protocol from the database built in the PACS server.

The capture direction of the object included in the capture protocol may include a coronal plane, a sagittal plane or a horizontal plane. Also, the pulse sequence to be used to capture the capture protocol may include, for example, continuation of a radio frequency (RF) pulse which may be repeatedly applied for capturing an MR image, and denote the order of capture based on the elapse of a capture time. Also, the capture time may include a time taken from a start time to an end time of the capture of a medical image, and may include a time remaining until the capture is completed.

The setting information before starting capture may include information (information related to a time remaining until starting to capture a medical image) related to a capture preparation time expended for an actual capture preparation and information related to a posture which an object needs to make before the medical image is captured. The setting information before starting capture may include information related to a breathing rate or a heart rate equal to or lower than a predetermined reference which is generally required for the object before starting the capture.

According to an exemplary embodiment, the content providing method may determine content to be provided to the object on the basis of the acquired information in operation S220.

For example, content for adjusting a breath pattern of an object may be determined based on information related to a breathing rate of the object. In response to the object breathing rapidly above a predetermined reference value, content for gradually stabilizing the breath pattern may be determined as content to be provided to the object. Content for adjusting a heart rate of the object may be determined based on information related to the heart rate of the object. A description on this will be made below with reference to FIGS. 3 to 5.

According to an exemplary embodiment, the determined content may be output in operation S230. The output content according to an exemplary embodiment may include at least one of an image, sound and text. For example, content to be provided to an object may be displayed on a screen in the form of certain images. Also, the content to be provided to the object may be output as sound, such as a voice, or the like, through a speaker, or the like.

Figure 3:
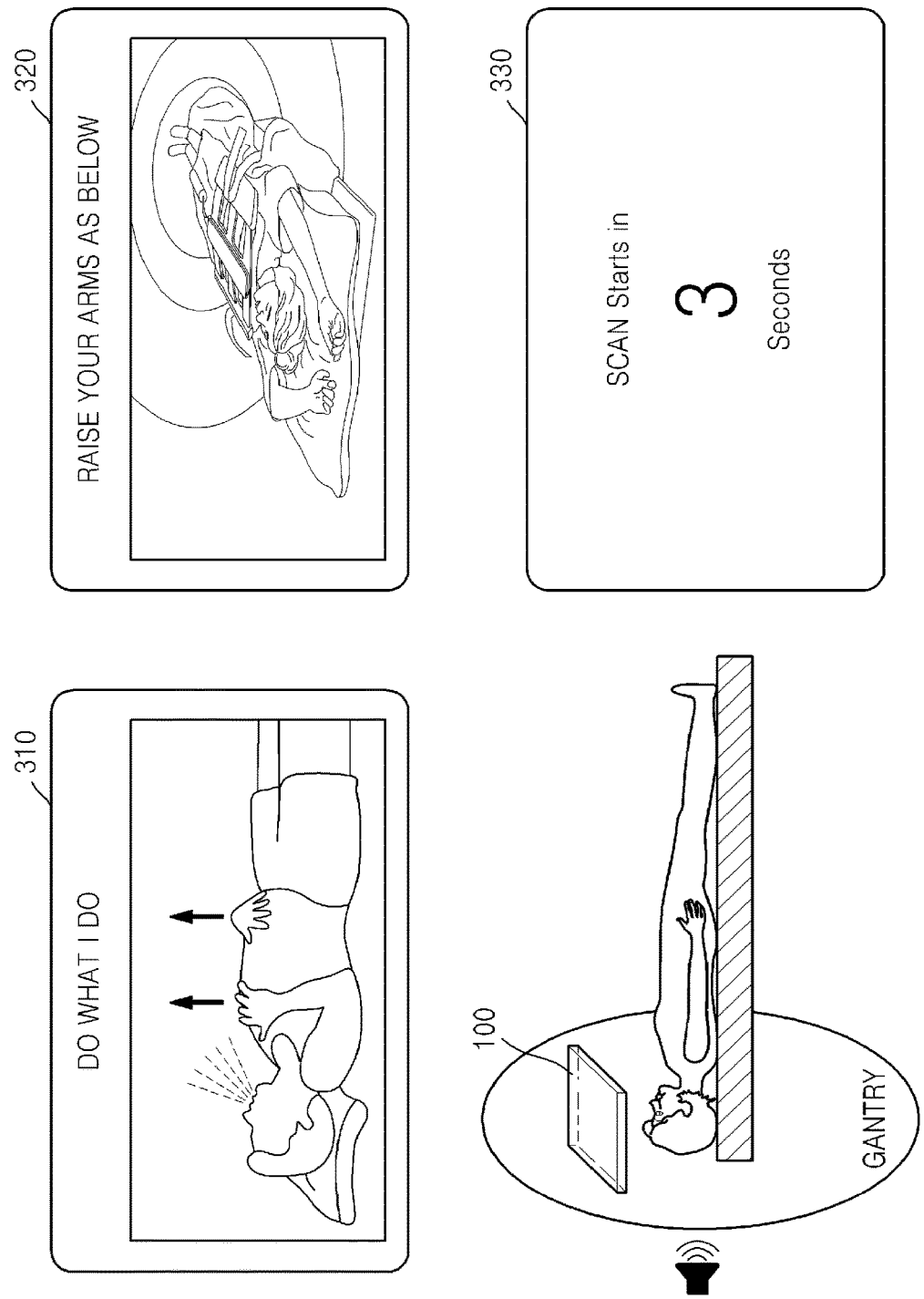
FIG. 3 illustrates a method of providing content to an object which is necessary for capture prior to starting the capture, according to an exemplary embodiment.

FIG. 3 illustrates a method of providing content necessary for capture to an object before starting the capture, according to an exemplary embodiment.

As illustrated in FIG. 3, the content providing apparatus 100 may select at least one of content 310 used to guide a breathing method of an object before starting capture, content 320 used to guide a posture of the object before starting the capture, and content 330 used to display a time remaining until starting the capture, on the basis of the setting information before starting capture.

The setting information before starting capture may include information related to the object, such as a physical disease, a mental disease, a captured part, a previous medical record, the number of capture experiences of a medical image, an age, and a sex of an object. The setting information before starting capture may include information related to capture, such as a capture protocol to be executed and a capture start time.

For example, in response to an object having a mental disease such as claustrophobia or panic disorder or has no capture experience of a medical image, as illustrated in FIG. 3, the content providing apparatus 100 may provide the content 310 used to guide a breathing method of the object or content for mental stability.

Moreover, in response to a posture of an object required for acquiring a good-quality medical image being predetermined (for example, abdomen capture, heart capture, etc.), as illustrated in FIG. 3, the content providing apparatus 100 may select and provide the content 320 used to guide the posture of the object.

Moreover, as illustrated in FIG. 3, before starting to capture a medical image, the content providing apparatus 100 may provide the content 330 used to display a time remaining until starting the capture.

Figure 4:
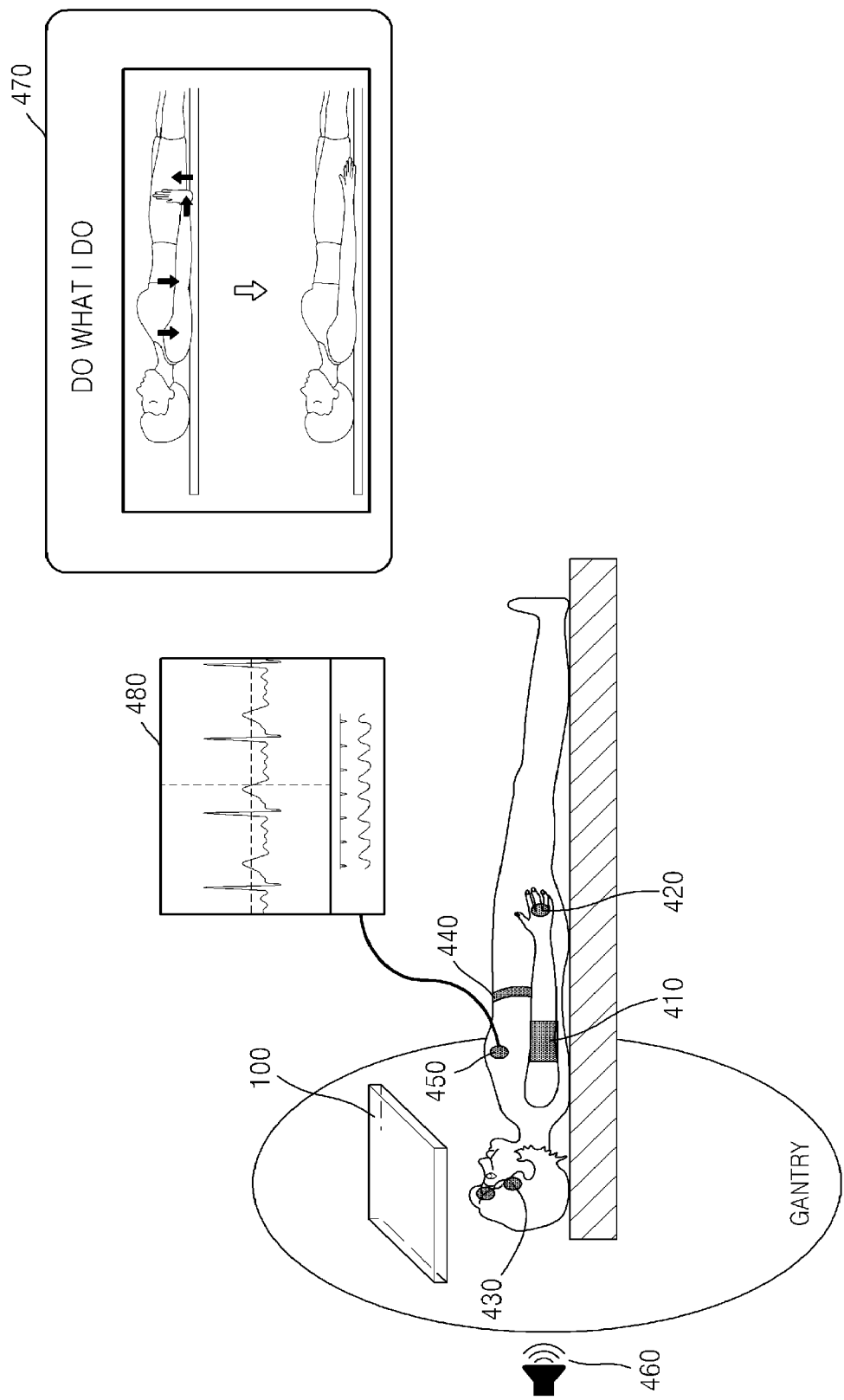
FIG. 4 illustrates a method of providing content on the basis of body information related to an object, according to an exemplary embodiment.

FIG. 4 illustrates a method of providing content on the basis of body information of an object, according to an related to capture embodiment.

As illustrated in FIG. 4, the content providing apparatus 100 may provide content 470 for mitigating stress of an object on the basis of body information related to the object.

The object may be in a state of tension due to a strange environment, noise of a medical apparatus, or an uncomfortable posture, in capturing a medical image. The object may receive stress due to an anxiety of exposure to radioactivity or a strong magnetic field for a long period of time. The stress increases a heart rate of the object, and increases a skin conductance response. The stress decreases a skin temperature of the object, decreases a ratio of an alpha wave among alpha wave and beta wave components of a brainwave, and stimulates a sympathetic system in order to increase a breathing rate of the object.

Stress which an object feels affects a result of a medical image. For example, in response to capturing a medical image of an abdomen or a heart, a motion caused by a heartbeat and breath of an object affects a result of the medical image. Therefore, in response to a heart rate or a breathing rate being increased by stress, a degree of capturing accuracy is reduced for the medical image of the abdomen or the heart.

Moreover, stress which an object experiences activates a specific part of the brain of the object. Therefore, in response to performing functional magnetic resonance imaging (fMRI) capture for capturing a function of the brain for a specific condition, it is difficult to accurately capture a brain activation region.

To this end, the content providing apparatus 100 monitors a heart rate, a skin conductance response, a body temperature, a brainwave, and breathing rate of an object, and in response to a determination that stress of the object increases, or in response to the object being in an excited state, the content providing apparatus 100 may select and provide content used to mitigate the stress of the object or content used to stabilize a heartbeat of the object.

The content providing apparatus 100 may measure a blood pressure, a body temperature, a brainwave, breath, or an ECG of an object which is collected with a blood pressure measurer 410, a body temperature measurer 420, a brainwave measurer 430, a breath measurer 440, and an ECG measurer 450. In response to a determination based on the measured body information of the object that stress of the object increases, or in response to a determination that a heart rate 480 of the object is equal to or higher than a predetermined reference value, the content providing apparatus 100 may provide content used to decrease the stress of the object or content used to stabilize a heartbeat of the object.

The content used to decrease the stress of the object or the content used to stabilize a heartbeat of the object may be audio content such as a sound of nature or a sound of meditation. Also, the content may be video content such as an image of a natural landscape. The video content may include a moving image such as gymnastics 470 for inducing a deep breath of the object or decreasing a heart rate.

Figure 5:
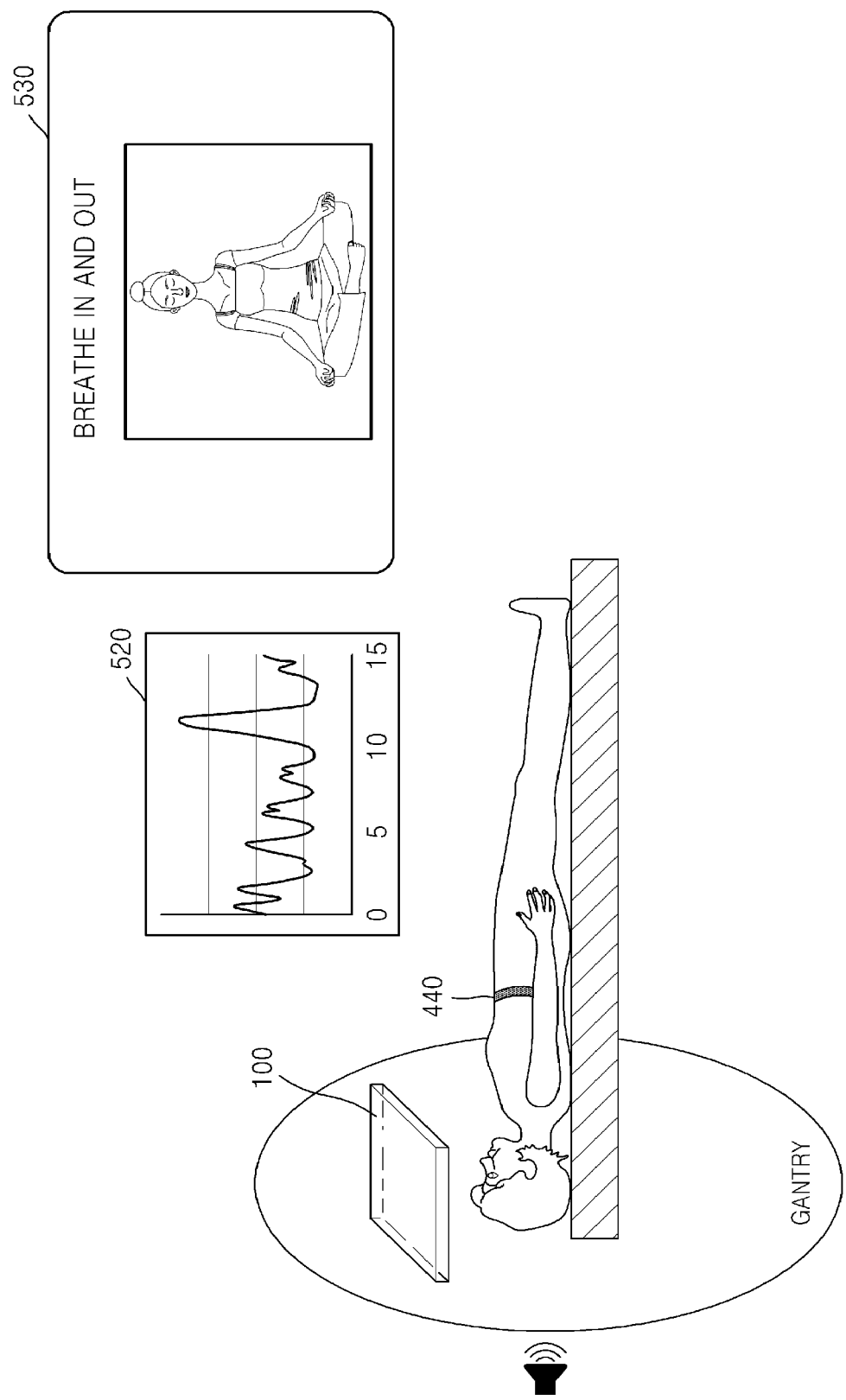
FIG. 5 illustrates a method of providing content used to stabilize a breath of an object, according to an exemplary embodiment.

FIG. 5 illustrates a method of providing content used to stabilize a breath of an object, according to an exemplary embodiment.

As illustrated in FIG. 5, when a breath of an object measured by the breath measurer 440 is irregular, the content providing apparatus 100 may select and provide content used to stabilize the breath of the object or content 530 used to guide the breath of the object.

The content providing apparatus 100 may receive information 520 related to the breath of the object from the breath measurer 440 attached to the object. In response to a determination that the breath of the object is irregular, the content providing apparatus 100 may determine content used to adjust the breath of the object because adjusting the breath of the object is required. In other words, the content providing apparatus 100 may provide the content used to stabilize the breath of the object or the content 530 used to guide the breath of the object.

The content providing apparatus 100 may continuously monitor the information 520 related to the breath of the object so as to stabilize the breath of the object, in the middle of capturing a medical image in addition to before capturing a medical image.

Figure 6:
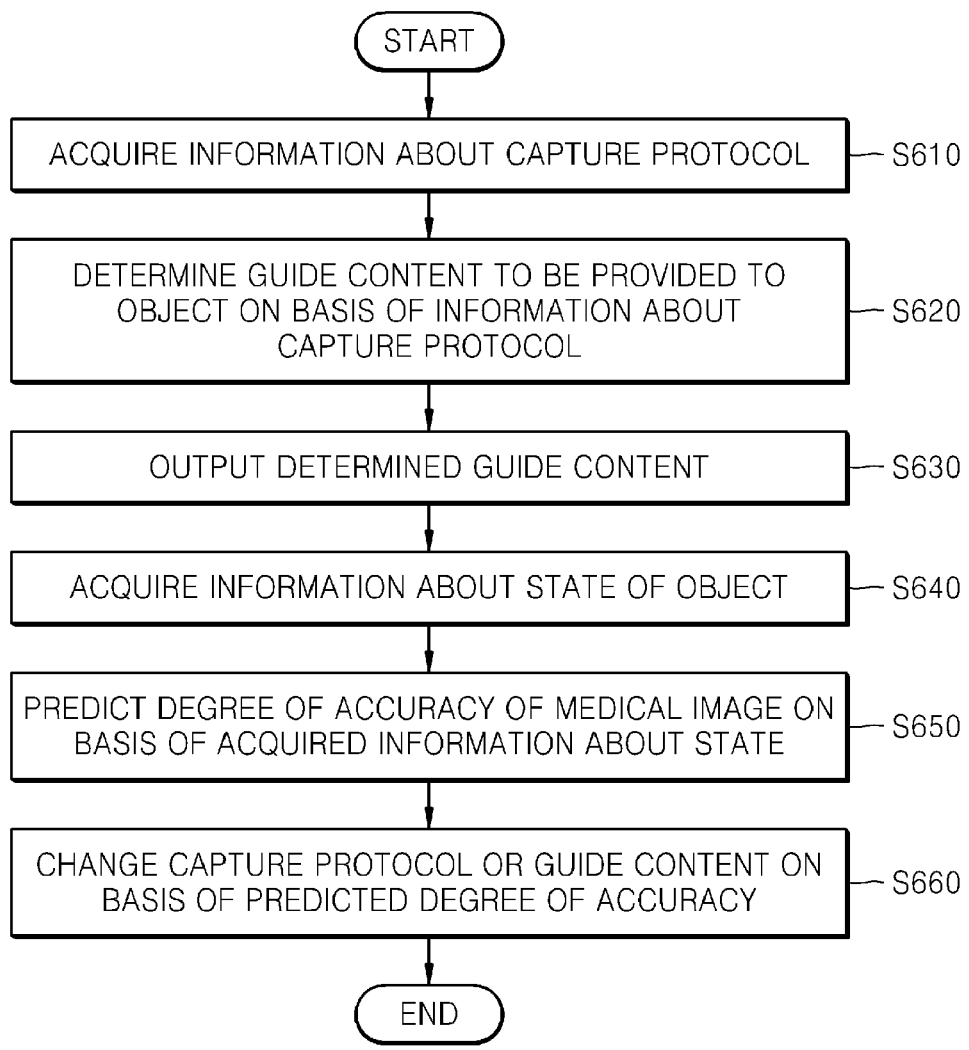
FIG. 6 is a flowchart of a method of changing a capture protocol or content to provide on the basis of information related to a state of an object, according to an exemplary embodiment.

FIG. 6 is a flowchart of a method of changing a capture protocol or content to provide on the basis of information related to a state of an object, according to an exemplary embodiment.

In operation S610, the content providing apparatus 100 may acquire information related to a capture protocol.

The capture protocol may include a captured part, a capture direction, a pulse sequence, and a parameter. The pulse sequence denotes continuation of an RF pulse that is repeatedly applied from an MRI apparatus to an object. The order of capture and a posture which the object needs to make may be determined according to the capture protocol.

The content providing apparatus 100, as described above, may receive from a database the information related to the capture protocol.

In operation S620, the content providing apparatus 100 may determine guide content to be provided to an object on the basis of the acquired information related to the capture protocol.

For example, the content providing apparatus 100 may select content used to guide a breath of the object according to execution of the capture protocol, in capturing a medical image of an abdomen or heart of the object. A description on this will be made below with reference to FIG. 7.

Moreover, the content providing apparatus 100 may select content used to guide a posture of the object according to the captured part or the capture direction. A description on this will be made below with reference to FIG. 8.

In operation S630, the content providing apparatus 100 may output the determined guide content. The output of the content is as described above with reference to FIG. 2, and thus, a detailed description thereof is not provided.

In operation S640, the content providing apparatus 100 may acquire information related to a state of the object.

The information related to the state of the object may denote a state of the object associated with the guide content which is output in operation S630. For example, in response to the guide content being content for guiding the breath or posture of the object, the acquired information related to the state of the object may be information related to the breath or posture of the object.

In operation S650, the content providing apparatus 100 may compare the state of the object with a state required by the guide content, and when a difference between the two states is equal to or greater than a certain range, the content providing apparatus 100 may determine a degree of accuracy of a medical image to be low.

For example, in capturing a medical image of the abdomen of the object, in response to content for guiding a breath according to the capture protocol being provided, the content providing apparatus 100 may receive information related to a breath state of the object to determine the breath state. In response to a determination that the received breath state and the guided state are similar to within a certain range, the content providing apparatus 100 may determine a degree of accuracy of the medical image of the abdomen to be high.

Moreover, in response to content for guiding a posture according to the capture protocol being provided, the content providing apparatus 100 may acquire information related to the posture of the object. In response to a determination that the guided posture and the acquired posture are similar to within a certain range, the content providing apparatus 100 may determine a degree of capturing accuracy to be high.

In operation S660, the content providing apparatus 100 may change the capture protocol or the guide content on the basis of the determined degree of accuracy.

In response to the degree of accuracy being determined as low, the content providing apparatus 100 may again execute a previously executed capture protocol. Alternatively, in response to the degree of accuracy being determined as low, the content providing apparatus 100 may change a capture protocol which enables the object to be more easily captured, and provide content based on the changed capture protocol. Alternatively, in response to the degree of accuracy being determined as high, the content providing apparatus 100 may change a current capture protocol to a capture protocol which has a higher degree of accuracy and enables quick capture, and provide content to the object which is used to induce a high-level breath stop time and posture.

For example, in response to a degree of capturing accuracy for the abdomen being determined as high, the content providing apparatus 100 may change a current capture protocol to a capture protocol which enables a larger quantity to be captured through a one-time scan, and provide content based on the changed capture protocol, thereby shortening a total capture time.

FIG. 7 illustrates a method of providing content used to guide a breath of an object according to a capture protocol, according to an exemplary embodiment.

In a general capture of an abdomen or a heart, artifacts may be added to a medical image due to a breath of an object. In order to reduce the number of artifacts, the object should stop a breath for several seconds to several minutes in capturing the abdomen or the heart. Generally, a user of a medical apparatus commands the object to stop a breath from a start to an end of a one-time scan.

As illustrated in FIG. 7, the content providing apparatus 100 may provide content 720 to 750 used to guide a breath to an object on the basis of a capture protocol for an abdomen or a heart.

Capture of a medical image of the abdomen or heart may include a plurality of scans. Therefore, the content providing apparatus 100 may provide content inducing stop of a breath, before one scan is started, and provide content inducing a convenient breath in response to the one scan being ended.

The content providing apparatus 100 may provide the content 720 that induces the object to stop a breath. The content providing apparatus 100 may provide a time for which the object should maintain a breath stop state according to the capture protocol. The content providing apparatus 100 may provide the content 730 that induces the object to breathe in or out.

Moreover, the content providing apparatus 100 may receive state information related to the breath of the object from the breath measurer 440, and provide a breath state as the content 740 of the object and information as the content 750 related to how well the object performs a required breathing method.

Moreover, as illustrated in FIG. 6, the content providing apparatus 100 may receive the state information related to the breath of the object from the breath measurer 440 to predict a degree of accuracy of an abdomen image of the object. The content providing apparatus 100 may change the capture protocol or the guide content on the basis of the predicted degree of accuracy.

FIG. 8 illustrates a method of providing content used to guide a posture of an object according to a capture protocol, according to an exemplary embodiment.

As illustrated in FIG. 8, the content providing apparatus 100 may provide content 810 indicating a posture which an object should make according to execution of a capture protocol.

Moreover, as described above with reference to FIG. 6, the content providing apparatus 100 may receive information related to the posture of the object from an image recognition apparatus to predict a degree of accuracy of a captured image of the object. The content providing apparatus 100 may change the capture protocol or guide content on the basis of the predicted degree of accuracy.

Figure 9:
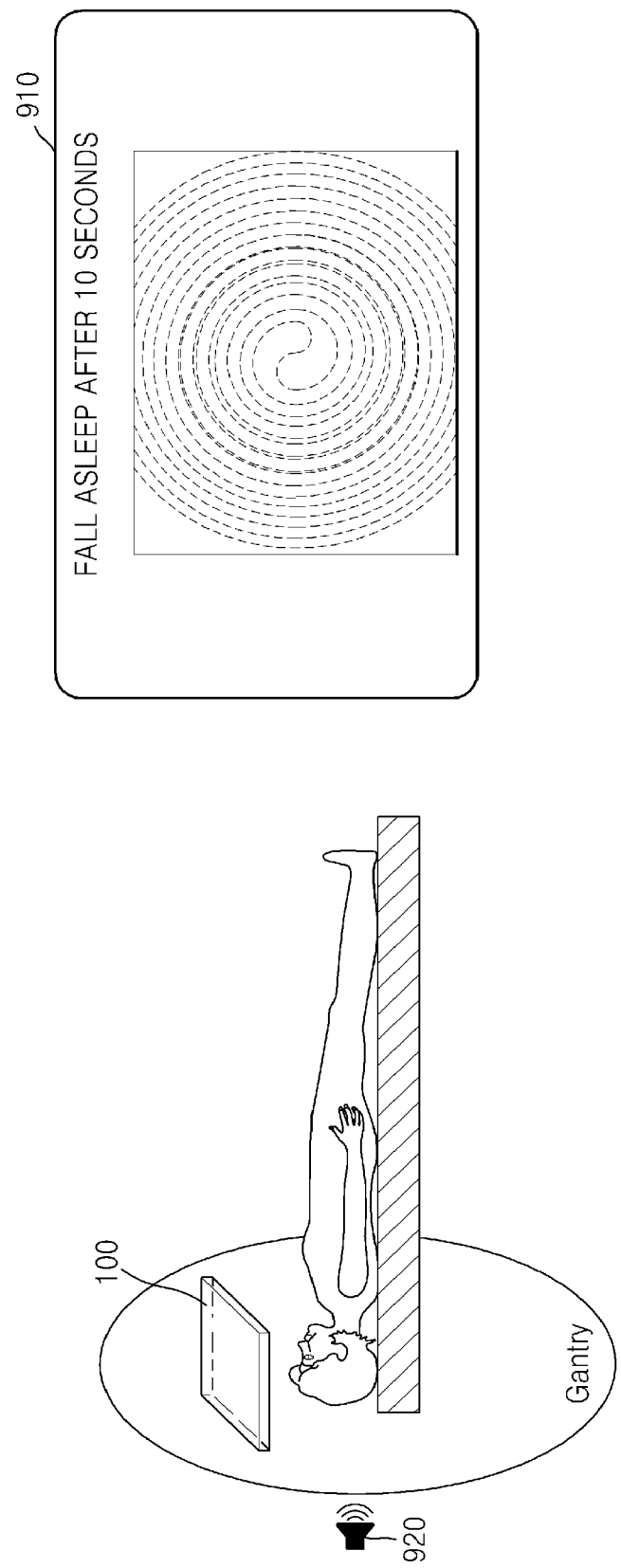
FIG. 9 illustrates a method of providing content used to induce sleep of an object, according to an exemplary embodiment.

FIG. 9 illustrates a method of providing content used to induce sleep of an object, according to an exemplary embodiment.

A patient or a child having claustrophobia or panic disorder may refuse or find it hard to undergo an MRI or CT capture in a narrow space. Due to this, a sleeping capture in which a sleeping pill is used is preferably performed.

As illustrated in FIG. 9, the content providing apparatus 100 may provide content for inducing sleep of an object. The content for inducing sleep may include a hypnosis image 910 for inducing the object to sleep or music 920 for inducing sleep.

Figure 10:
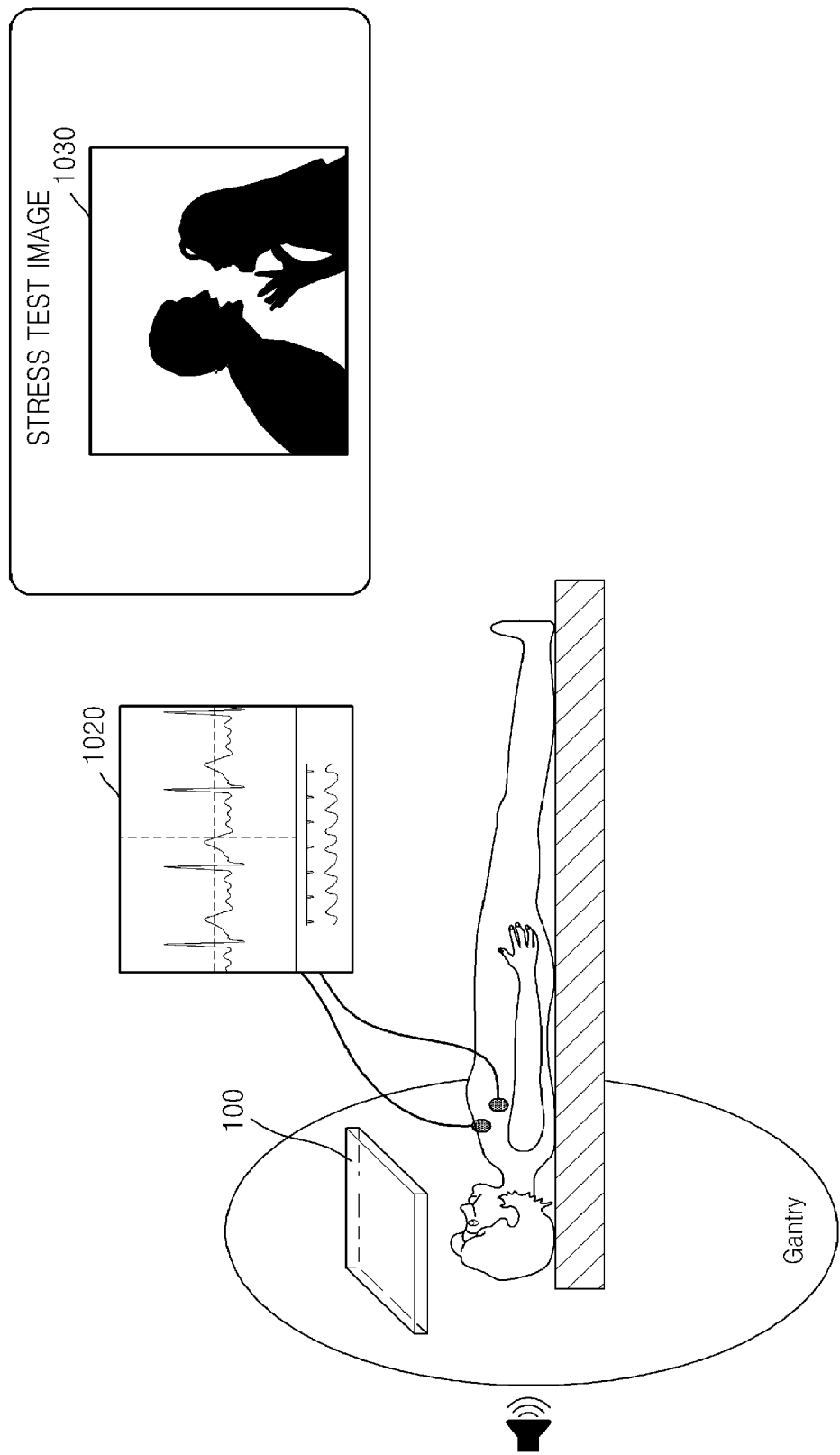
FIG. 10 illustrates a method of providing content used to test stress, according to an exemplary embodiment.

FIG. 10 illustrates a method of providing content used to test stress, according to an exemplary embodiment.

As illustrated in FIG. 10, the content providing apparatus 100 may provide content for increasing a heart rate of an object or content for causing mental stress of the object.

In a patient, who is not able to perform physical exercise or is unable to increase a heart rate to a predetermined reference through exercise, a heart stress test using drugs may be performed. In response to a certain level of stress being applied to a human body, a mental stress test for sensing a physical change may be performed.

The content providing apparatus 100 may provide content to the object, enabling the stress test.

The content providing apparatus 100 may determine the content to provide on the basis of a heart state 1020 of the object that is measured by the ECG measurer 450. For example, in response to the heart rate of the object being equal to or lower than a predetermined reference, the content providing apparatus 100 may provide content 1030 for more increasing the heart rate of the object.

FIG. 11 illustrates a method of providing content for fMRI capture, according to an object embodiment.

As illustrated in FIG. 11, the content providing apparatus 100 may provide fMRI test content on the basis of an fMRI capture protocol and a response of an object.

The content providing apparatus 100 may provide fMRI content on the basis of the fMRI capture protocol. For example, in a case of fMRI that captures an activity region the brain that is associated with a recognition ability of the object, the content providing apparatus 100 may provide content to the object, used to stimulate a recognition sense of the object.

Moreover, the content providing apparatus 100 may provide the fMRI content on the basis of the response of the object.

For example, the content providing apparatus 100 may receive a brainwave of the object from a brainwave measurer 1110, and provide the fMRI test content on the basis of the received brainwave. The content providing apparatus 100 may analyze the received brainwave to determine a degree of emotional stability or a degree of concentration of the object, and provide suitable content 1120 on the basis of the brainwave information.

Moreover, the content providing apparatus 100 may recognize a voice of the object or an image of the object, and provide the fMRI test content on the basis of the recognized voice or image. For example, the content providing apparatus 100 may provide a question type of test content to the object, and recognize the voice of the object in order to acquire a response. The content providing apparatus 100 may determine fMRI test content to be subsequently executed, on the basis of a response acquired from the object. The content providing apparatus 100 may recognize a motion or posture of the object, and determine fMRI test content 1130 on the basis of the recognized motion or posture.

FIG. 12 illustrates a method of providing content related to an object while capturing a medical image, according to an exemplary embodiment.

As illustrated in FIG. 12, the content providing apparatus 100 may provide content associated with an object to the object. The content associated with the object may include information about a disease of the object, information about a captured part, and a previous medical record of the object.

In FIG. 12, in response to the disease of the object being cerebral infarction, the content providing apparatus 100 may provide information 1210 related to the cerebral infarction or content 1220 for preventing the cerebral infarction.

Figure 13:
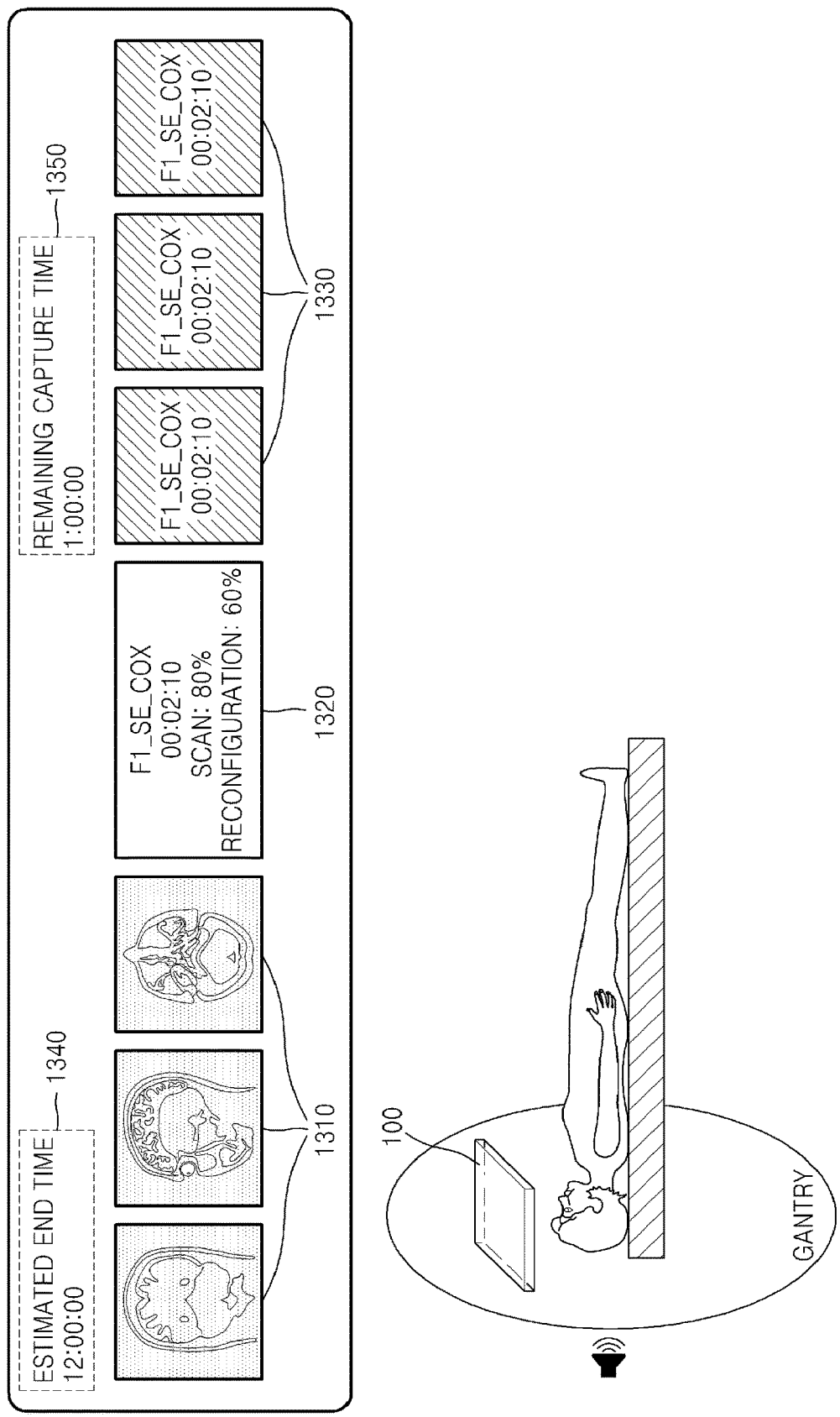
FIG. 13 illustrates a method of providing information to an object which is related to the capture of a medical image, according to an to an object embodiment.

FIG. 13 illustrates a method of providing information related to the capture of a medical image to an object, according to an to the object embodiment.

As illustrated in FIG. 13, the content providing apparatus 100 may provide information related to a medical image, which is being currently captured, to an object while capturing the medical image.

For example, the content providing apparatus 100 may provide a capture protocol 1320 which is being currently executed, a capture protocol 1330 to be executed later, a currently captured part, information related to a currently captured slice, an estimated end time 1340 of capture, a time 1350 remaining until the capture is ended, and information related to a capture protocol including the order of capture. Also, the content providing apparatus 100 may provide a medical image 1310 of an object for which capture is completed to date.

The content providing apparatus 100 may display a pulse sequence as information related to current capture, and display a degree of execution of capture for a currently captured slice image.

The content providing apparatus 100 may provide content to the object associated with a general medical image capture operation such as an MRI or a CT capture. The content providing apparatus 100 may provide content to the object associated with a cause of noise which occurs in an MRI capture.

Moreover, the content providing apparatus 100 may provide entertainment content, such as music, a movie, a game, and the Internet, to the object in capturing a medical image.

The content providing apparatus 100 according to an exemplary embodiment may recognize a voice of the object to provide content based on a condition.

For example, the content providing apparatus 100 may analyze a voice tone of the object in order to analyze an emotional state of the object in fMRI capture, and provide content used to test a function of the brain on the basis of the analyzed emotional state. The content providing apparatus 100 may analyze previous and next contexts of the recognized voice to provide fMRI content suitable for the object's intent in the fMRI capture.

The content providing apparatus 100 according to an exemplary embodiment may analyze a specific gesture of the object to select content to be provided to the object.

In capturing a medical image, a posture of an object is fixed, and a motion of the object is limited. Therefore, it is difficult for the object to control content provided by the content providing apparatus 100. Accordingly, the content providing apparatus 100 may recognize a gesture of the object, and provide content to the object on the basis of the recognized gesture.

For example, the content providing apparatus 100 may recognize a specific hand motion of an object, or recognize a motion of an eyeball of the object, thereby receiving a content control signal from the object. Also, the content providing apparatus 100 may recognize a specific motion of the feet, the head, or fingers as well as the hands or the eyes, thereby receiving the content control signal from the object.

The content providing apparatus 100 according to an exemplary embodiment may recognize a facial expression of an object to select content to be provided to the object. The content providing apparatus 100 may recognize the facial expression of the object to determine a current emotional state and a degree of inconvenience which the object experiences in capture. Therefore, the content providing apparatus 100 may provide entertainment content or content (which is used to increase the understanding of a currently captured medical image) for capture of the medical image on the basis of the determined emotional state or degree of inconvenience of the object.

Figure 14:
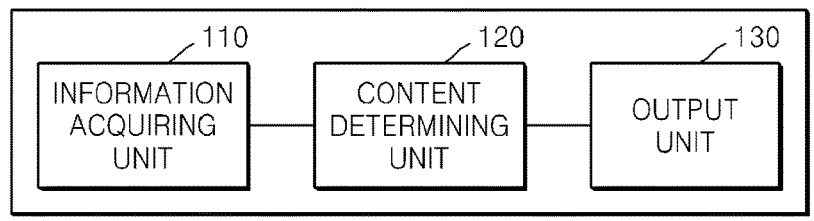
FIG. 14 illustrates a content providing apparatus for providing to an object information related to the capture of a medical image, according to an exemplary embodiment.

FIG. 14 illustrates a content providing apparatus 100 for providing information related to the capture of a medical image to an object, according to an exemplary embodiment.

The content providing apparatus 100 according to an exemplary embodiment may include an information acquiring unit 110, e.g., an information acquirer, a content determining unit 120, e.g., a content determiner, and an output unit 130, e.g. an output.

Figure 15:
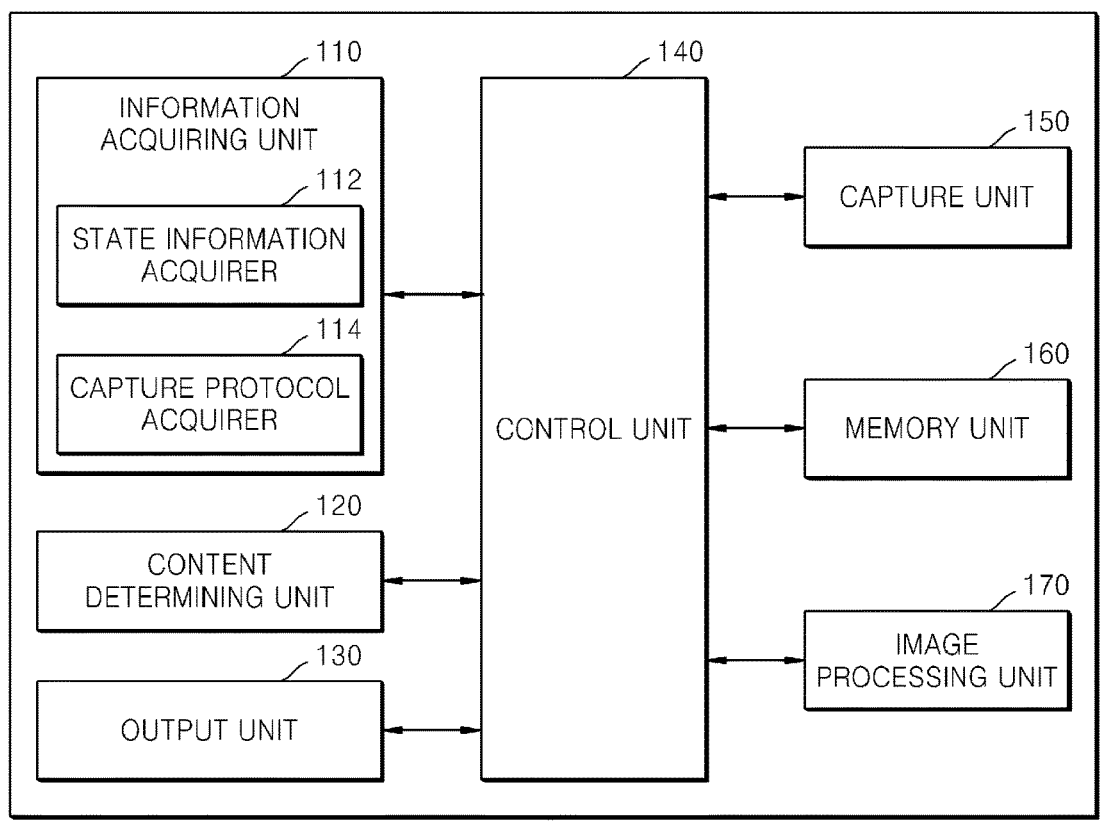
FIG. 15 illustrates a content providing apparatus for providing to an object information related to the capture of a medical image, according to another exemplary embodiment.

FIG. 15 illustrates a content providing apparatus for providing information related to the capture of a medical image to an object, according to another exemplary embodiment.

As illustrated in FIG. 15, the content providing apparatus 100 may further include a control unit 140, e.g., a controller, a capture unit 150, e.g., a capturer, a memory unit 160, e.g., a memory and an image processing unit 170, e.g., an image processor.

The information acquiring unit 110 according to an exemplary embodiment may include a state information acquirer 112, which acquires information related to a state of an object, and a capture protocol acquirer 114 that acquires information related to a capture protocol.

However, the illustrated elements are not all essential elements. The content providing apparatus 100 may be implemented with more or less elements than the number of illustrated elements.

Hereinafter, the elements will be described sequentially.

The state information acquirer 112 may acquire information related to a state of an object.

The state information acquirer 112 may include at least one of a temperature sensor that senses a body temperature of an object, a blood pressure sensor that senses a blood pressure of the object, an ECG measurer (ECG electrodes) that senses a heart state of the object, a respiratory monitoring bellows that senses a breath state of the object, a brainwave measurer (EEG electrodes) that senses a brainwave of the object, and an MRI apparatus that captures an MR image of the object.

The state information acquirer 112 may include an electromyogram (EMG) measurer, an electrooculogram (EOG) measurer, an electroretinogram (ERG) measurer, a galvanic skin response (GSR) measurer, and a phonocardiogram (PCG) measurer.

Moreover, the state information acquirer 112 may include at least one of a voice recognition sensor, which recognizes a voice of an object, and an image recognition sensor that recognizes a posture and motion of the object.

The capture protocol acquirer 114 may acquire a capture protocol used to capture the object. The capture protocol acquirer 114 may acquire the capture protocol from a memory included in the content providing apparatus 100. Also, the capture protocol acquirer 114 may acquire the capture protocol from a picture archiving and communication system (PACS) server, an electronic medical record (EMR) server, a personal health record (PHR) server, or a radiology information system (RIS) server.

The content determining unit 120, e.g., a content determiner, may determine content to be provided to the object, on the basis of the acquired information.

The content determining unit 120 may determine the content to be provided to the object, on the basis of at least one of information about the acquired state of the object and information about the capture protocol.

The output unit 130 may output the determined content.

The output unit 130 may be included in a medical image capturing apparatus that captures a medical image of the object. For example, the output unit 130 may be disposed at an inner wall of a gantry of an MRI apparatus or a CT apparatus. Also, the output unit 130 may be disposed in a bore of the MRI apparatus or the CT apparatus.

Moreover, the output unit 130 may be an element that is movable according to a position of the object. For example, the content providing apparatus 100 may automatically adjust a position of the output unit 130 according to the object's view.

The output unit 130 is for outputting an audio signal or a video signal, and may include a display unit, e.g., a display, such as a screen, or a sound output unit such as a speaker.

The display unit may display and output information obtained through processing by the content providing apparatus 100. For example, the display unit may display a user interface (UI) or a graphical user interface (GUI) associated with content.

Moreover, the display unit may display a UI or a GUI associated with an operation of a medical image capturing apparatus, and display a medical image.

In addition, the display unit may include at least one of a liquid crystal display (LCD), a thin film transistor-liquid crystal display, an organic light-emitting diode (OLED) display, a flexible display, a 3D display, an electrophoretic display, and a transparent display.

Moreover, the content providing apparatus 100 may include at least one or more display units depending on an implementation type of the content providing apparatus 100.

The sound output unit may output audio data. Also, the sound output unit may receive a content-related acoustic signal from the content providing apparatus 100. The sound output unit may include a speaker and a buzzer.

The control unit 140, e.g., a controller, according to an exemplary embodiment may control the information acquiring unit 110, the content determining unit 120, the output unit 130, the control unit 140, the capture unit 150, e.g., the capturer, the memory unit 160, e.g., memory, and the image processing unit 170, e.g., the image processor.

The capture unit 150 may receive a signal, which is transferred from the object or passes through the object, to collect data used to acquire a medical image. The image processing unit 170 may generate a medical image of the object by using the data collected by the capture unit 150.

The capture unit 150 or the image processing unit 170 may include an MRI apparatus, a CT apparatus, or an X-ray apparatus.

The memory unit 160 may store content related to the capture of a medical image, and store information related to the state of the object or information about a capture protocol. The memory unit 160 may include at least one type of storage medium of a flash memory, a hard disk, a multimedia micro card, a card type memory (a secure digital (SD) card, an extreme digital (XD) card, or the like), random access memory (RAM), static random access memory (SRAM), read-only memory (ROM), an electrically erasable programmable read-only memory (EEPROM), and a programmable read-only memory (PROM).

The content providing apparatus 100 may include a communicator (not shown). The communicator may include a wireless communicator, a short-distance communicator, and a wired communicator. The content providing apparatus 100 may receive information related to the capture of a medical image or object-related content from an external server through the communicator (not shown).

The content providing apparatus 100 may include a user input unit, e.g., user input (not shown). The user input unit (not shown) may denote a means for inputting data used for a user to control the content providing apparatus 100. For example, the user input unit may include a keypad, a dome switch, a touch pad (for example, a contact capacitive type, a press resistive type, an infrared sensing type, a surface ultrasonic conductive type, an integration tension measurement type, and a piezo effect type), a jog wheel, and a jog switch, but is not limited thereto.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments of the present invention have been described with reference to the figures, it will be understood by those of ordinary skill in the art that various changes in form and details may be made therein without departing from the spirit and scope of the present invention as defined by the following claims.

What is claimed is:

1. A method of providing, by a magnetic resonance imaging (MRI) apparatus, content to a subject in capturing a magnetic resonance (MR) image of the subject, the method comprising:
    acquiring information of capture protocols;
    controlling to apply radio frequency pulses to the subject, based on the acquired information of the capture protocols, to capture the MR image; and
    controlling to display the content comprising an indication of a capture protocol that is currently executed, an indication of a ratio of execution of the capture protocol that is currently executed, and an indication of a capture protocol to be executed later, based on the acquired information of the capture protocols,
    wherein the indication of the capture protocol that is currently executed and the indication of the capture protocol to be executed later are displayed according to an order of the capture protocols, and the capture protocol that is currently executed is different than the capture protocol to be executed later.

2. The method of claim 1, wherein the indication of the ratio of the capture protocol that is currently executed is displayed in the indication of the capture protocol that is currently executed.

3. The method of claim 1, further comprising providing the subject with the content as an acoustic signal.

4. The method of claim 1, wherein the displayed content further comprises a plurality of indications of capture protocols to be executed later, and
    wherein the indication of the capture protocol that is currently executed and the plurality of indications of the capture protocols to be executed later are displayed separately.

5. The method of claim 1, wherein the displayed content further comprises an image of a natural landscape.

6. The method of claim 1, wherein the displayed content further comprises a time of capturing the MR image.

7. The method of claim 1, wherein each of the capture protocols denotes continuation of a radio frequency pulse that is repeatedly applied to capture the MR image.

8. The method of claim 1, further comprising determining the content, based on the acquired information of the capture protocols,
wherein the controlling to display comprises controlling to display, to the subject, the determined content.

9. A non-transitory computer-readable storage medium storing a program that causes a processor to perform the method of claim 1.

10. A magnetic resonance imaging (MRI) apparatus for providing content to a subject in capturing a magnetic resonance (MR) image of the subject, the apparatus comprising:
a memory storing instructions;
a processor configured to execute the instructions to:
acquire information of capture protocols; and
control to apply radio frequency pulses to the subject, based on the acquired information of the capture protocols, to capture the MR image; and
control to display the content comprising an indication of a capture protocol that is currently executed, an indication of a ratio of execution of the capture protocol that is currently executed, and an indication of a capture protocol to be executed later, based on the acquired information of the capture protocols,
wherein the indication of the capture protocol that is currently executed and the indication of the capture protocol to be executed later are displayed according to an order of the capture protocols, and the capture protocol that is currently executed is different than the capture protocol to be executed later.

11. The MRI apparatus of claim 10, wherein the indication of the ratio of the capture protocol that is currently executed is displayed in the indication of the capture protocol that is currently executed.

12. The MRI apparatus of claim 10, further comprising a speaker configured to provide the subject with the content as an acoustic signal.

13. The MRI apparatus of claim 10, wherein the displayed content further comprises a plurality of indications of capture protocols to be executed later, and
wherein the indication of the capture protocol that is currently executed and the plurality of indications of the capture protocols to be executed later are displayed separately.

14. The MRI apparatus of claim 10, wherein the displayed content further comprises an image of a natural landscape.

15. The MRI apparatus of claim 10, wherein the displayed content further comprises a time of capturing the MR image.

16. The MRI apparatus of claim 10, wherein each of the capture protocols denotes continuation of a radio frequency pulse that is repeatedly applied to capture the MR image.

17. The MRI apparatus of claim 10, wherein the controller is further configured to:
determine the content, based on the acquired information of the capture protocols; and
control to display, to the subject, the determined content.

18. A magnetic resonance imaging (MRI) apparatus for providing content to a subject in capturing a magnetic resonance (MR) image of the subject, the apparatus comprising:
a memory storing instructions;
a processor configured to execute the instructions to:
acquire information of an order of capture protocols, and information of a ratio of execution of the capture protocols;
control to apply radio frequency pulses to the subject, based on the acquired information of the order of the capture protocols and the acquired information of the ratio of execution of the capture protocols, to capture the MR image;
control to display the content comprising an indication of a ratio of execution of each of the capture protocols, based on the acquired information of the order of the capture protocols and the acquired information of the ratio of execution of the capture protocols, wherein the indication of the ratio of execution of each of the capture protocols is displayed according to the order of the capture protocols and displayed separately; and
control to update the displayed indication of the ratio of execution of each of the capture protocols.

19. The MRI apparatus of claim 18, further comprising a sound output interface configured to provide the subject with the content as an acoustic signal.

20. The MRI apparatus of claim 18, wherein the displayed content further comprises an image of a natural landscape.

* * * * *